US011944448B2

(12) United States Patent
Xu et al.

(10) Patent No.: US 11,944,448 B2
(45) Date of Patent: Apr. 2, 2024

(54) ADAPTIVE ILLUMINATION APPARATUS, METHOD, AND APPLICATIONS

(71) Applicant: Cornell University, Ithaca, NY (US)

(72) Inventors: Chris Xu, Ithaca, NY (US); Kriti Charan, Freeville, NY (US); Bo Li, Ithaca, NY (US); Michael Buttolph, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/960,805

(22) Filed: Oct. 5, 2022

(65) Prior Publication Data

US 2023/0039098 A1 Feb. 9, 2023

Related U.S. Application Data

(63) Continuation of application No. 16/344,157, filed as application No. PCT/US2017/061801 on Nov. 15, 2017, now Pat. No. 11,607,165.

(Continued)

(51) Int. Cl.
*A61B 5/00* (2006.01)
*G02B 21/00* (2006.01)
*H01S 3/067* (2006.01)

(52) U.S. Cl.
CPC .............. *A61B 5/40* (2013.01); *A61B 5/0071* (2013.01); *G02B 21/0032* (2013.01); *H01S 3/06754* (2013.01); *G01N 2201/0697* (2013.01)

(58) Field of Classification Search
CPC ....... A61B 5/40; A61B 5/0071; A61B 5/0075; A61B 2562/0233; A61B 5/00;

(Continued)

(56) References Cited

U.S. PATENT DOCUMENTS

| 5,530,582 A | 6/1996 | Clark |
| 5,847,863 A | 12/1998 | Galvanauskas et al. |

(Continued)

FOREIGN PATENT DOCUMENTS

| JP | 10073851 | 3/1998 |
| JP | 2014524662 | 9/2014 |

(Continued)

OTHER PUBLICATIONS

Ozden, Ilker, et al., "Identification and Clustering of Even Patterns from In Vivo Multiphoto Optical Recordings of Neuronal Ensembles", Journal of neurophysiology, vol. 100, No. 1, Jul. 1, 2008.

*Primary Examiner* — Md M Rahman
(74) *Attorney, Agent, or Firm* — Barnes & Thornburg LLP (57) ABSTRACT

A system and method for adaptive illumination, the imaging system comprising an excitation source having a modulator, which generates a pulse intensity pattern having a first wavelength when the excitation source receives a modulation pattern. The modulation pattern is a data sequence of a structural image of a sample. An amplifier of the imaging system is configured to receive and amplify the pulse intensity pattern from the modulator. A frequency shift mechanism of the imaging system shifts the first wavelength of the pulse intensity pattern to a second wavelength. A laser scanning microscope of the imaging system receives the pulse intensity pattern having the second wavelength.

19 Claims, 12 Drawing Sheets

Related U.S. Application Data (60) Provisional application No. 62/422,268, filed on Nov. 15, 2016.

(58) Field of Classification Search
CPC .......... G02B 21/0032; G02B 2207/114; G02B 21/0076; G02B 21/361; H01S 3/06754; G01N 2201/0697
USPC ........................................................ 356/300
See application file for complete search history.

(56) References Cited

U.S. PATENT DOCUMENTS

| | | | |
|---|---|---|---|
| 10,588,694 B1* | 3/2020 | Neev .................... | A61B 18/203 |
| 2007/0215816 A1* | 9/2007 | Hui ........................ | G01N 21/65 |
| | | | 372/6 |
| 2010/0086251 A1* | 4/2010 | Xu ........................ | G02F 1/3513 |
| | | | 385/1 |
| 2010/0284585 A1 | 11/2010 | Wang et al. | |
| 2011/0292047 A1* | 12/2011 | Chang ................... | G06V 30/268 |
| | | | 345/424 |
| 2015/0192768 A1* | 7/2015 | Salem .................... | G01N 21/47 |
| | | | 250/227.2 |

FOREIGN PATENT DOCUMENTS

| | | |
|---|---|---|
| WO | 2005094275 | 10/2005 |
| WO | 2014205413 | 12/2014 |

* cited by examiner

ADAPTIVE ILLUMINATION APPARATUS, METHOD, AND APPLICATIONS

CROSS-REFERENCE TO RELATED APPLICATIONS

This application is a continuation of co-pending U.S. patent application Ser. No. 16/344,157, filed Apr. 23, 2019, that is a U.S. National Phase filing of International Application No. PCT/US17/61801, filed Nov. 15, 2017, which claims priority to U.S. Provisional Patent application No. 62/422,268, filed Nov. 15, 2016 each of which is hereby incorporated by reference in its entirety.

FIELD OF THE INVENTION

The present disclosure is directed generally to a smart laser source, and more particularly to a system and method for adaptive illumination based on the sample under study.

BACKGROUND

In the field of neuroscience, the detection and understanding of neural activity is critical in diagnosing diseases and other disorders and researching treatments or cures to such diseases and disorders. For example, studying rhythmic patterns of neural activity, neural oscillations, can be used to diagnose tremors, such as those indicating Parkinson's disease, migraines, and epilepsy. When new treatments are developed and tested, neural activity can be studied to determine if the proposed treatment is safe and effective. Individual neurons are also studied at the cellular and molecular levels to analyze the interaction of the neuron with other cells. Studying individual neurons in varying regions of the brain provides insights into cognition and sensory perception functions of the brain. As the brain is estimated to have billions of neurons, which are dense and difficult to differentiate. As numerous neurons in close proximity fire rapid action potentials, high-speed imaging is required to capture neural activity.

For volumetric recording of a large number of neurons, high imaging speed is necessary. Conventional multiphoton microscopes (MPMs) operate at the photon shot-noise limit, which limits the number of neurons that can be imaged at high spatial and temporal resolution. Particularly, signal photons (i.e. the signal-to-noise ratio (SNR)) determined by the maximum permissible average and peak power in biological specimens limit the maximum number of neurons that can be imaged. One method to increase the imaging speed is to only image the region of interest (ROI).

3D random access MPM (RAMP) is used to enable high-speed imaging of 3D volumes of large number of neurons. Acousto-optic deflectors (AODs) are used to position the laser beam in 3D. The somas of the neurons are illuminated with significant dwell times for recording the neuronal activity. In one example, neurons only comprise approximately 10% of the volume of the mouse brain, so an order of magnitude improvement in imaging speed can be achieved compared to conventional raster scanning. RAMP is the fastest conventional method for imaging large neurons simultaneously in scattering tissue. Nevertheless, RAMP suffers several significant shortcomings.

The field-of-view of RAMP is small and typically less than 200 µm in X, Y and Z. The optical setup for RAMP is expensive and complex, requiring four large-aperture AODs and four relay telescopes for the scanning system. The deflection efficiency of the AOD is poor, typically less than 70% for each AOD at approximately 800 nm. At the long wavelength windows of 1300 nm and 1700 nm, the efficiency of AOD is much worse due to material limitations. Due to these difficulties, RAMPs have only seen limited deployment in neuroscience research, and all RAMPs were performed at a wavelength less than 1.06 µm.

Accordingly, there is a need for a system and method to improve the speed of recording large numbers of neurons.

SUMMARY OF THE INVENTION

The present disclosure is directed to inventive methods for adaptive illumination.

According to one aspect of the invention is an imaging system for adaptive illumination comprising an excitation source having a modulator, which generates a pulse intensity pattern having a first wavelength when the excitation source receives a modulation pattern. The modulation pattern is a data sequence of a structural image of a sample. An amplifier of the imaging system is configured to receive and amplify the pulse intensity pattern from the modulator. A frequency shift mechanism of the imaging system shifts the first wavelength of the pulse intensity pattern to a second wavelength. A laser scanning microscope of the imaging system receives the pulse intensity pattern having the second wavelength.

According to an embodiment, the frequency shift mechanism of the imaging system is a SSFS.

According to an embodiment, the SSFS of the imaging system is in a photonic crystal rod.

According to an embodiment, the sample is a neuron.

According to an embodiment, the excitation source is an all-fiber chirped pulse amplifier.

According to an embodiment, the modulator is an electro-optic modulator.

According to one aspect of the invention is a method for adaptive illumination, the method comprising the steps of: (i) generating a high-resolution structural image of a sample; (ii) processing the high-resolution structural image to determine one or more regions of interest; (iii) converting the regions of interest into a data sequence representing a modulation pattern having a first wavelength; (iv) transmitting the modulation pattern to an excitation source; (v) encoding, at the excitation source, the modulation pattern in time; (vi) amplifying the modulation pattern with an amplifier at the excitation source; (vii) shifting the first wavelength of the modulation pattern to a second wavelength; and (viii) transmitting the modulation pattern having the second wavelength to a laser scanning microscope.

According to an embodiment, the method further includes the step of conducting a raster scan of a sample.

According to an embodiment, the amplifier is an Erbium-doped-fiber amplifier.

According to an embodiment, the excitation source is chirped pulse amplifier.

According to an embodiment, the regions of interest are defined by somas of the neuron.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

The present disclosure is directed to embodiments of a method and system for adaptive illumination.

Figure 1:
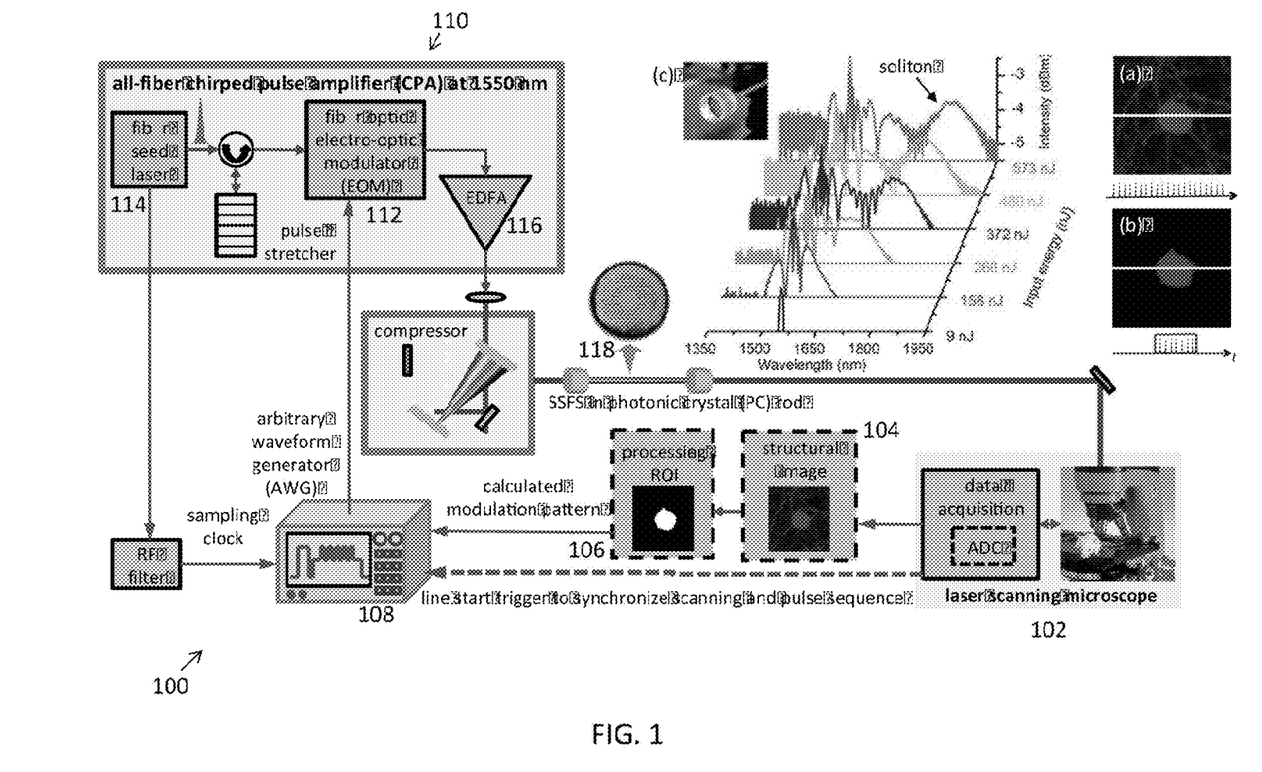
FIG. 1 is a schematic representation of an imaging system for adaptive illumination, in accordance with an embodiment.

According to one embodiment, the disclosure is directed to an imaging system for adaptive illumination. Referring first to FIG. 1, there is shown a schematic representation of an imaging system 100 for adaptive illumination, in accordance with an embodiment. The system 100 comprises a laser scanning microscope 102 for raster scanning of a sample. Raster scanning of the sample produces a high-resolution structural image 104. Image processing is then performed on the high-resolution structural image 104 to determine regions of interest (ROIs) 106. For recording the activity of neurons, the ROIs 106 are defined by the regions of the somas of the neurons. After determining the ROIs 106, the ROI 106 information is converted to a digital sequence, a calculated modulation pattern. The calculated modulation pattern is then used to control an arbitrary waveform generator (AWG) 108, which drives an excitation source 110.

In the depicted embodiment, the excitation source 110 is an all-fiber chirped pulse amplifier (CPA). Conventional CPAs are widely known and used for amplifying fs pulses to high energies without the associated nonlinear effects, such as self-focusing, photodissociation, and UV-light production. However, conventional CPAs use a pulse picker to uniformly remove the pulses and obtain a desired repetition rate. The embodiment of the CPA 110 in FIG. 1 comprises a fiber optic electro-optic modulator (EOM) 112, which imposes a desired pulse intensity pattern on a low power fiber seed laser 114 having a high repetition rate (e.g., >20 MHz). Thus, the EOM 110 encodes the pulse intensity pattern in time.

Still referring to FIG. 1, the CPA 110 also comprises a fiber amplifier 116. In the depicted embodiment, the fiber amplifier 116 is an Erbium-doped-fiber amplifier (EDFA). The EDFA 116 receives and amplifies the resulting modulated pattern (i.e., pulse train). As the EDFA 116 has a long excited state lifetime, intensity modulation at $100s$ of KHz will have no impact on the average output power of the EDFA 116, which is how fiber amplifiers are utilized in telecommunications to amplify data impulses. In some aspects, the proposed excitation source 110 behaves like a telecommunications transmitter transmitting the image of the ROIs 106. The amplified pulses typically range from 1 to 4 µJ/pulse depending on the effective repetition rate, and are then compressed back to approximately 400 fs in a compressor.

The imaging system 100 of FIG. 1 also comprises a soliton self-frequency shift (SSFS) 118. The SSFS shifts the wavelength from 1550 nm to approximately 1700 nm. In the depicted embodiment, the SSFS 118 is shown in a large mode area photonic crystal (PC) rod 118, which is achieved by controlling the launch power. In the embodiment shown, the SSFS 118 is capable of generating wavelength tunable solitons from 1600 nm to close to 2000 nm, as shown as (c) in FIG. 1. The images (a) and (b) in FIG. 1 are images resulting from a conventional laser source (i.e., uniform pulse train) and the imaging system 100 described herein, respectively. The solitons have short pulse width and high pulse energy for 3PE. For 2PM with adaptive illumination as described herein, the pulses can be frequency doubled using SHG crystals, such as BiBo and KNBO, to the range of 800 nm to 1000 nm.

The pulse intensity pattern is then transmitted from the SSFS 118 to the laser scanning microscope 102, a multiphoton microscope (MPM) 102 in the depicted embodiment. The synchronization of scanning and the pulse intensity pattern ensure that the excitation beam will only illuminate the somas. Thus, all the permissible laser power is focused on the ROIs 106 and the laser is essentially "turned off" outside the ROIs 106. Through the laser power concentration, the signal generation and resulting imaging speed is increased by the inverse of the volume fraction of the ROI 106. Localized labeling of the cells further enhances the increased speed. An example of a localized label is a nucleus label, which provides more precise laser power concentration, increasing the imaging speed. This method can be used to simultaneously image thousands of neurons in deep cortical layers of subjects, such as mice and rats, without degrading the temporal resolution and signal-to-noise ratio (SNR). In addition, the method can be used to simultaneously image tens of thousands of neurons through the depth of a single cortical column with simultaneous 2PM (shallow) and 3PM (deep).

The above embodiments describe 3PM at the 1700 nm spectral window and 2PM at 800 nm-1000 nm. In an alternative embodiment, the method is executed at the 1300 nm window. Because the proposed pulse modulation scheme is compatible with all amplified laser systems, fiber or solid state, the method may be translated to the 1300 nm window. In the 1300 nm embodiment, a 1300 nm excitation source 102 may utilize a CPA 110 to pump an optical parametric amplifier (OPA). A nearly identical modulation scheme may be used to control the pulse pattern of the CPA 110, which subsequently generates the desired pulse train at the 1300 nm in the OPA.

In another embodiment, "unwanted" pulses are removed before the final power amplifier (i.e., the EDFA 116). While modulation of laser power using an EOM 112 or AOM has been done routinely in the past, e.g., for beam blanking or enhancing dynamic range, the modulation is always performed after the laser output (i.e., outside the laser). By placing the modulator (EOM) 112 inside the imaging system 100, the imaging system 100 not only allows a high speed, low power (i.e., only required to handle <100 mW), and low cost (~$1k) fiber optic modulator (EOM) 112 to perform the intensity modulation, but also enables the entire output power of the fiber amplifier (EDFA) 116 to be used. It is estimated that an EDFA 116 with ~5 W output power is sufficient for the subsequent SSFS 118. Such an amplifier is commercially available and can be routinely made in a university lab. In contrast, placing the modulator (EOM) 112 outside the imaging system 100 would necessitate an EDFA 116 with ~50 W output (e.g., neurons occupy ~10% of the volume of the mouse brain). Such a high power amplifier would be a major challenge to the current state-of-the-art, and totally impractical for neuroscience applications.

In an alternative embodiment, each ROI 106 may also comprise a guard band. The guard band is built around the ROI 106 and used to eliminate motion artifact resulting from imaging awake or behaving animals (or other samples). The size of the guard band may be determined based at least in part on the range of motion measured during the image session. That way, the size of guard band is tailored to the RMS value of the motion to eliminate the vast majority of the motion artifact without significantly comprising the efficiency of the illumination. In one embodiment, the guard band may also be used to easily detect systematic drift. Thus, the microscope may receive real-time feedback of the sample drift, which allows it to track the sample drift.

Figure 2:
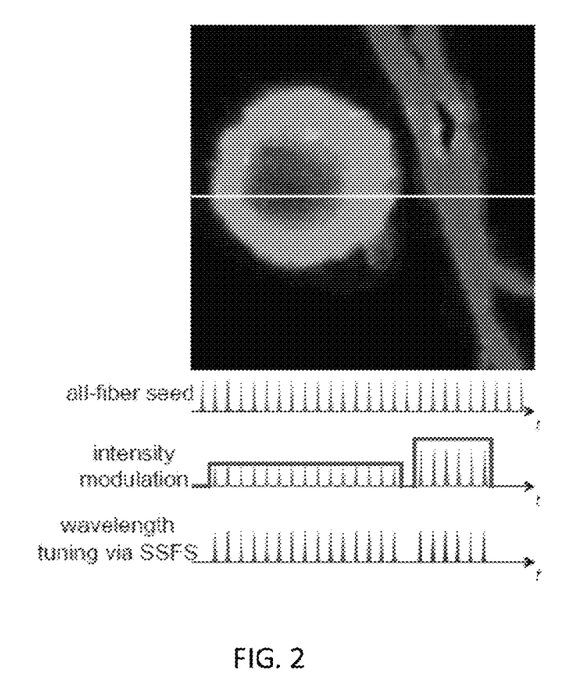
FIG. 2 is a graph of results from wavelength tuning using SSDFS, in accordance with an embodiment.

Referring now to FIG. 2, there is shown a graph of results from wavelength tuning using SSFS 118, in accordance with an embodiment. Adaptive wavelength tuning may be executed using SSFS 118 (as shown in FIG. 1). Using SSFS 118 allows for faster wavelength tuning than conventional tuning using a mode-locked laser (e.g., single box Ti:S laser). Wavelength tuning across the 1700 nm spectral window for 3PE can be achieved on a pulse-to-pulse time scale using the EO intensity modulator. The combination of adaptive intensity modulation and wavelength tuning ensures the most efficient illumination for samples with multiple fluorescent markers with significant spectral separations.

Figure 3:
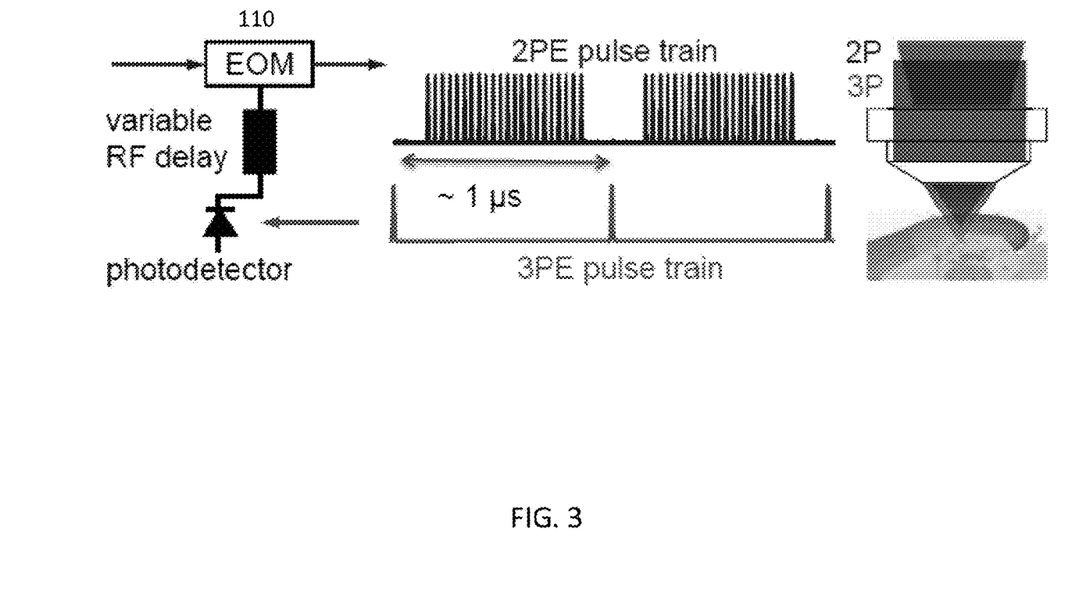
FIG. 3 is a chart of a method of multiplane imaging, in accordance with an embodiment.

Referring now to FIG. 3, there is shown a chart of a method of multiplane imaging, in accordance with an embodiment. In the depicted embodiment, concurrently 2PE and 3PE (two-photon excitation microscopy and three-photon excitation microscopy) and are used to simultaneously measure neural activity from both shallow and deep cells. In one example, deep cells include scattering tissue, which is approximately 1 mm in a mouse brain. Through simultaneous activity recording with 2PE and 3PE, the number of neurons studied in each region may be maximized. In the embodiment shown in FIG. 3, time division multiplexing 2PE and 3PE laser beams, which are spatially offset to have two separate focal planes after the objective, permit simultaneous activity recording.

In the depicted embodiment, the 2PE beam is switched to the "on" position only during the time between two adjacent 3PE pulses. The 2PE beam is switched to the "on" position by intensity modulation with an EOM 112, which is driven with an RF signal derived from the 3PE pulse train using a photodetector, as shown. A sample is alternatively (within approximately 1 µs) illuminated either by the 2PE or the 3PE beam. The 2- and 3-photon excited fluorescence signals are separated in time according to the recorded 3PE laser pulse train with a post-processing software.

For imaging deep cells (e.g., into scattering tissue), the optimum repetition rate for a 3PE source is approximately 1 MHz due to the high peak power needs. The optimal repetition rate for 2PM at shallower depths is approximately 10-50 times higher. The significant difference in pulse repetition rates allows parallel 2- and 3-photon imaging without the need to synchronize the excitation pulse trains. Synchronizing the excitation pulse trains is often difficult and thus, the method is more efficient without it. Still referring to FIG. 3, through removal of occasional "conflicting" pulses (e.g., using a pulse picker) from the 2PE source, which comprise approximately 1-10% of the pulses, a minimum offset between excitation pulses of tens of ns can be ensured, which is sufficient for more fluorophores (e.g., the fluorescence lifetime for many GCaMPs is approximately 3 ns). Therefore, simultaneous 2- and 3-photon imaging can be achieved for the same fluorophore just by correlating the detected fluorescence signal with the appropriate excitation source (as shown in FIG. 3). Once again, such an intensity modulation can be done before the final power amplifier stage, enabling efficient and robust operation. One of the benefits of simultaneous use of 2- and 3-photon excitation comes when the lasers are focused in different planes. Simply controlling the divergence of the beam entering the objective back aperture can provide hundreds of micrometers of focal plane shift without significant imaging performance degradation (e.g., FOV and resolution).

Figure 4A:
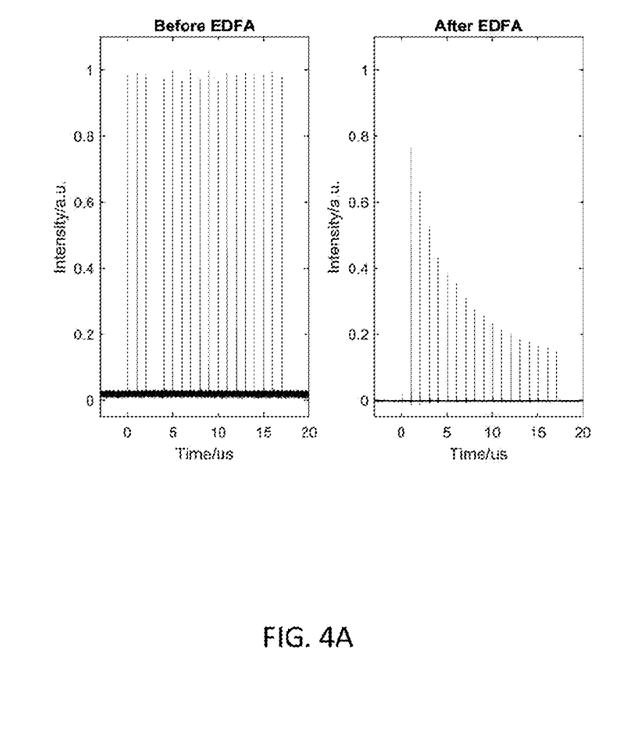
FIG. 4A is a pre-EDFA graph and post-EDFA graph showing pulse energy of output pulses over time.
Figure 4B:
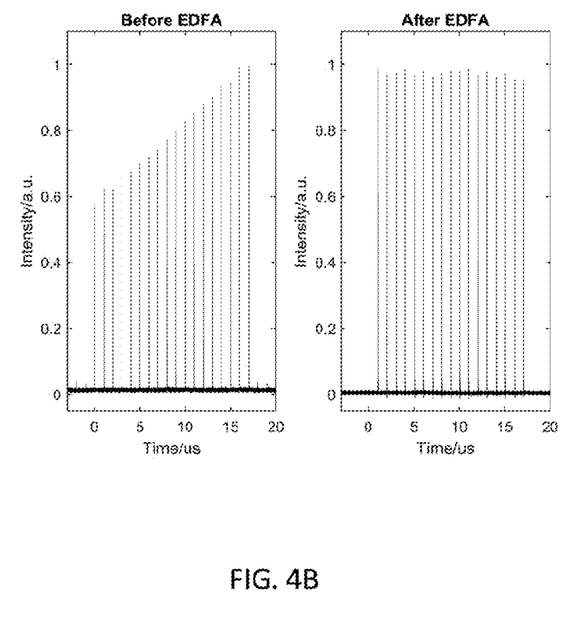
FIG. 4B is the pre-EDFA graph and post-EDFA graph from FIG. 4A with the data pre-shaped.

Referring now to FIGS. 4A-11, there are shown various graphs and charts illustrating the proof of concept for the imaging system for adaptive illumination. Referring first to FIGS. 4A and 4B, there is shown the pulse energy of output pulses over time. When a uniform pulse train is sent through the EDFA 116, the output pulses have different pulse energy due to the EDFA 116 gain transient. In FIG. 4A, the pre-EDFA uniform pulse train is shown on the left and the post-EDFA output pulses are shown on the right. It has been proved in the field of telecommunications and fiber laser source that this problem can be solved by pre-shaping the input, as shown in our measured data. The data shown in FIG. 4A has been pre-shaped, resulting in the graphs in FIG. 4B. Specifically, in FIG. 4B, the pre-shaped uniform pulse train pre-EDFA is shown on the left and the pre-shaped output pulses post-EDFA is shown on the right. However, when the input pulse train has a complicated temporal distribution, the definition of pre-shaping waveform will be impossible.

Figure 5:
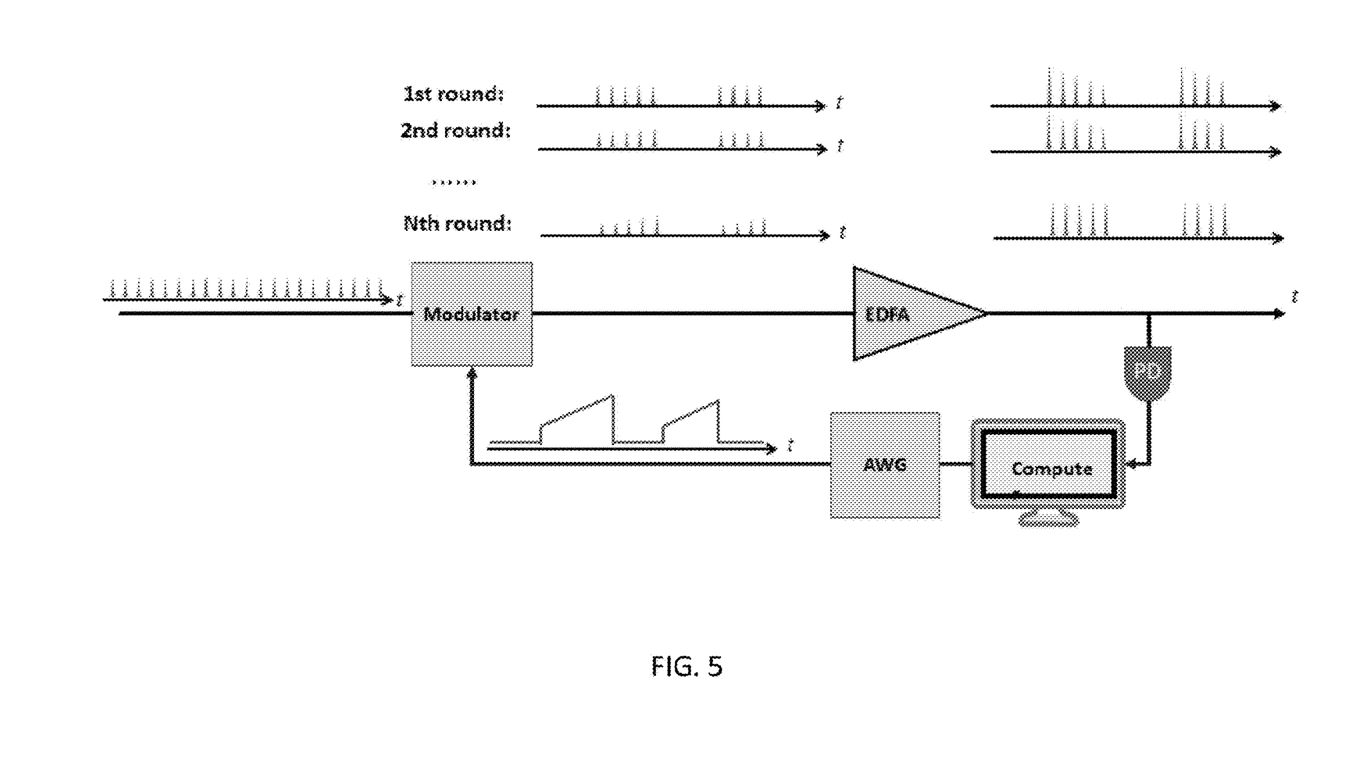
FIG. 5 is a diagram of a feedback loop for flattening the output pulse train when it is passed from the EOM to the EDFA, in accordance with an embodiment.

In order to facilitate pre-shaping with an input pulse train having a complicated temporal distribution, a feedback loop configuration can flatten the output pulse train. In an exemplary embodiment, shown in FIG. 5, the input pulse train is flattened each time it is passed from the EOM 112 to the EDFA 116. The input pulse train will be flattened a 1st round, a 2nd round, and an Nth round until the output pulse train is flat. In one embodiment, the flattening process may require several tens of rounds.

Figure 6:
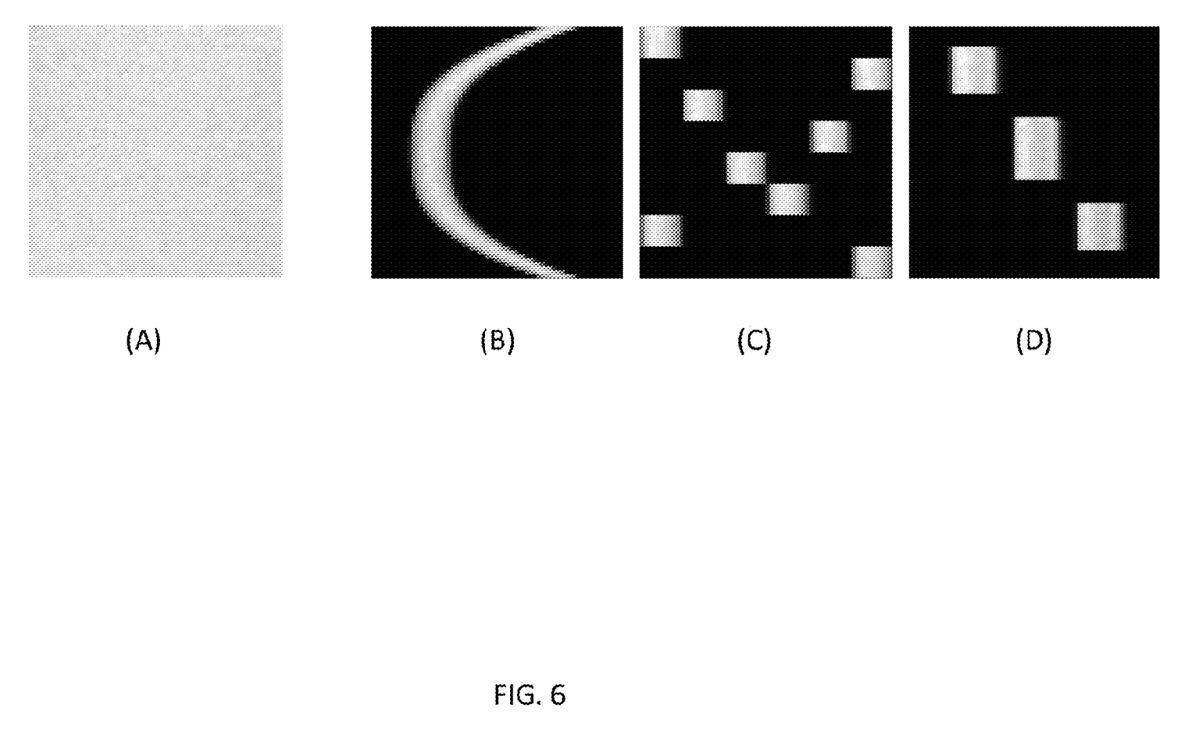
FIGS. 6A, 6B, 6C, and 6D show a first data set of images resulting from use of the imaging system and method for adaptive illumination, in accordance with an embodiment.

Referring now to FIG. 6, there is shown a first data set of images resulting from use of the imaging system 100 and method for adaptive illumination described herein. The results shown in FIG. 6 were produced with fluorescein dye pool and an Olympus microscope. Image (A) in FIG. 6 is an image produced according to conventional method (i.e., without the imaging system 100 and method for adaptive illumination disclosed herein). Images (B), (C), and (D) were obtained using the disclosed imaging system 100 and method for adaptive illumination (AI). As can be derived from the measurements shown in Tables 1 below, AI resulted in a power improvement factor of approximately 10.

TABLE 1

Comparative Imaging Measurements

|  | Uniform (without AI) | Non-uniform (with AI) |
| --- | --- | --- |
| Power on sample | 1.7 mW | 0.16 mW |

TABLE 1-continued

Comparative Imaging Measurements

|  | | |
| --- | --- | --- |
| Effective repetition rate | 1 MHz | ~0.1136 MHz |
| Brightness (mean pixel value) | 872.914 | 854.455 |

|  | Calculated Improvement | Measured Improvement |
| --- | --- | --- |
| Power (assuming same brightness) | ~8.8 | 10.5 |
| Brightness (assuming same average power) | ~77.5 | ~110.5 |

Figure 7:
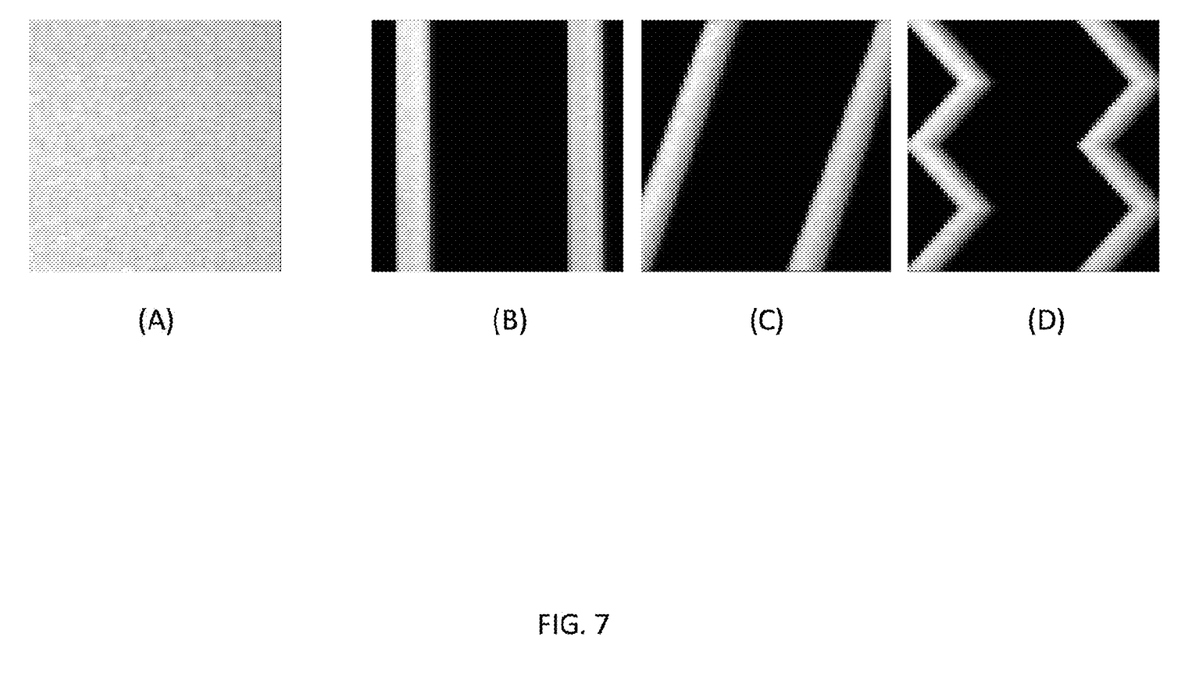
FIGS. 7A, 7B, 7C, and 7D show a second data set of images resulting from use of the imaging system and method for adaptive illumination, in accordance with an embodiment.

Referring now to FIG. 7, there is shown a second data set of images resulting from use of the imaging system 100 and method for adaptive illumination described herein. The results shown in FIG. 7 were produced with fluorescein dye pool and an Olympus microscope. Image (A) in FIG. 7 is an image produced according to conventional method (i.e., without the imaging system 100 and method for AI disclosed herein). Images (B), (C), and (D) were obtained using the disclosed imaging system 100 and method for AI. As can be derived from the measurements shown in Tables 2 below, AI resulted in a power improvement factor of approximately 6.

TABLE 2

Comparative Imaging Measurements

|  | Uniform (without AI) | Non-uniform (with AI) |
| --- | --- | --- |
| Power on sample | 1.9 mW | 0.48 mW |
| Effective repetition rate | 1 MHz | ~0.2 MHz |
| Brightness (mean pixel value) | 545 | 1272 |

|  | Calculated Improvement | Measured Improvement |
| --- | --- | --- |
| Power (assuming same brightness) | ~5 | 6 |
| Brightness (assuming same average power) | ~25 | ~36 |

Figure 8:
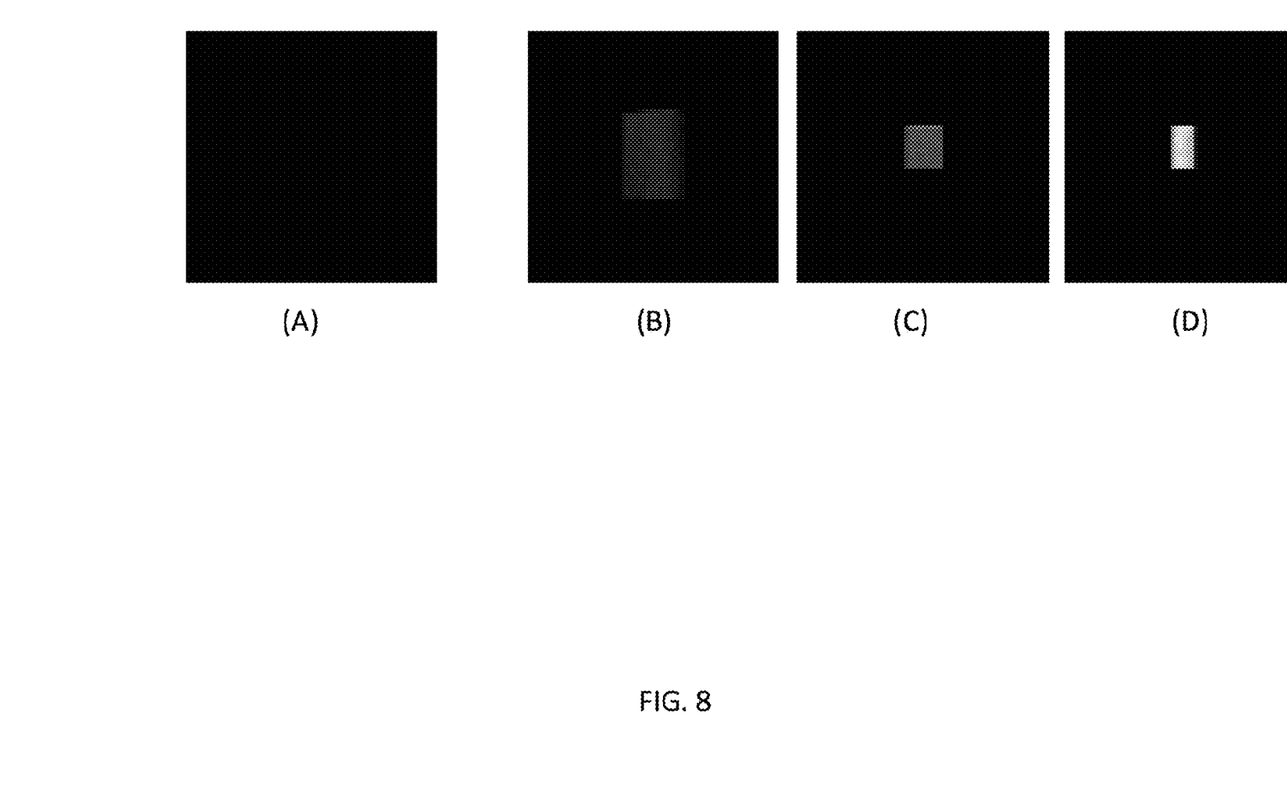
FIGS. 8A, 8B, 8C, and 8D are a third data set of images resulting from use of the imaging system and method for adaptive illumination, in accordance with an embodiment.

Referring now to FIG. 8, there is shown a third data set of images resulting from use of the imaging system 100 and method for adaptive illumination described herein. The results shown in FIG. 8 were produced with fluorescein dye pool and an Olympus microscope. Image (A) in FIG. 8 is an image produced according to conventional method (i.e., without the imaging system 100 and method for AI disclosed herein). Images (B), (C), and (D) were obtained using the disclosed imaging system 100 and method for AI. As can be derived from the measurements shown in Tables 3 below, AI resulted in a brightness improvement factor of approximately 23, 41, and 100, respectively.

TABLE 3

Comparative Imaging Measurements

|  | Uniform (without AI) | Non-uniform 1 (with AI) | Non-uniform 2 (with AI) | Non-uniform 3 (with AI) |
| --- | --- | --- | --- | --- |
| Power on sample | 0.32 mW | 0.32 mW | 0.32 mW | 0.32 mW |
| Laser repetition rate | 1 MHz | 1 MHz | 1 MHz | 1 MHz |
| Effective repetition rate | 1 MHz | 0.25 MHz | 0.156 MHz | 0.094 MHz |
| Pixel value (mean value of the bright area) | 9.619 | 222.6 | 402.272 | 1042.111 |
| Measured improvement factor |  | 23 | 42 | 100 |
| Theoretical improvement factor |  | 16 | 41 | 114 |

Figure 9:
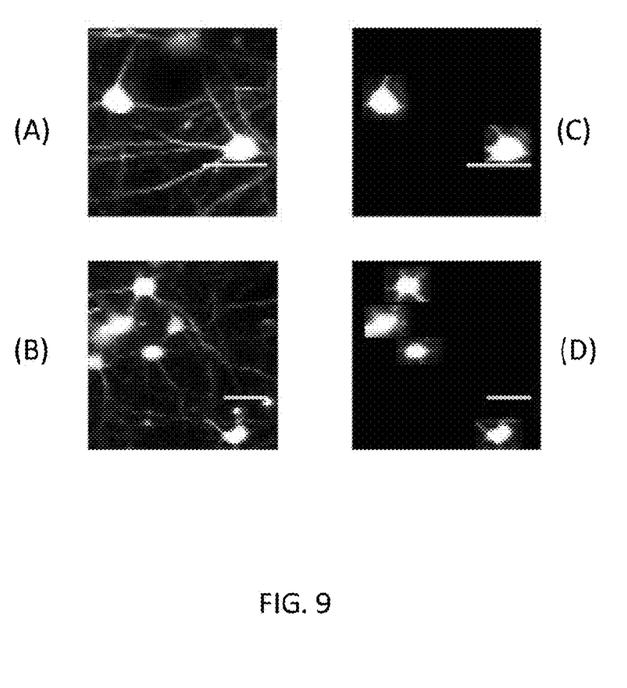
FIGS. 9A, 9B, 9C, and 9D show a fourth data set of images resulting from use of the imaging system and method for adaptive illumination, in accordance with an embodiment.

Referring now to FIG. 9, there is shown a fourth data set of images resulting from use of the imaging system 100 and method for adaptive illumination described herein. The results shown in FIG. 9 were produced with neurons (YFP) and an Olympus microscope. Images (A) and (C) are at a depth of 338 μm, while images (B) and (D) are at a depth of 320 μm. Images (A) and (B) were produced according to conventional method (i.e., without the imaging system 100 and method for AI disclosed herein) with 4.32 mW on the sample. Images (C) and (D) were obtained using the disclosed imaging system 100 and method for AI with 0.88 mW on the sample. The use of AI resulted in a power improvement factor of approximately 4.36.

Figure 10:
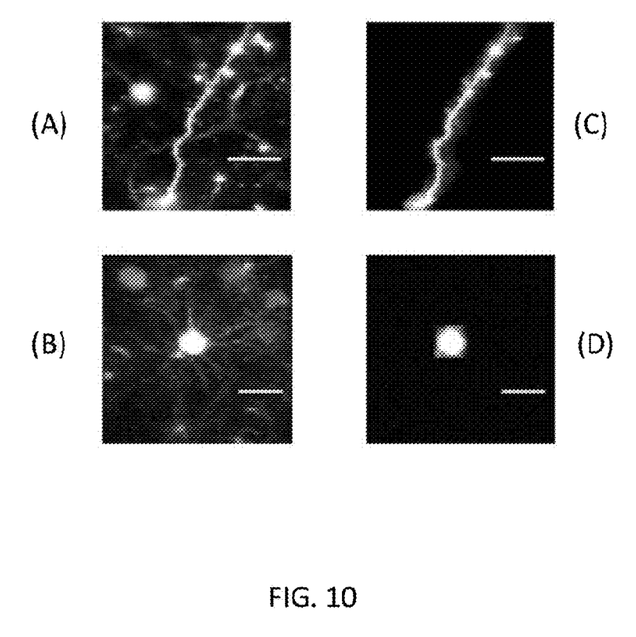
FIGS. 10A, 10B, 10C, and 10D show a fifth data set of images resulting from use of the imaging system and method for adaptive illumination, in accordance with an embodiment.

Referring now to FIG. 10, there is shown a fifth data set of images resulting from use of the imaging system 100 and method for adaptive illumination described herein. The results shown in FIG. 10 were produced with neurons (YFP) and an Olympus microscope. Images (A) and (C) are at a depth of 306 μm, while images (B) and (D) are at a depth of 649 μm. Images (A) and (B) were produced according to conventional method (i.e., without the imaging system 100 and method for AI disclosed herein) with 3.84 mW on the sample. Images (C) and (D) were obtained using the disclosed imaging system 100 and method for AI with 0.56 mW on the sample. The use of AI resulted in a power improvement factor of approximately 6.85.

Figure 11:
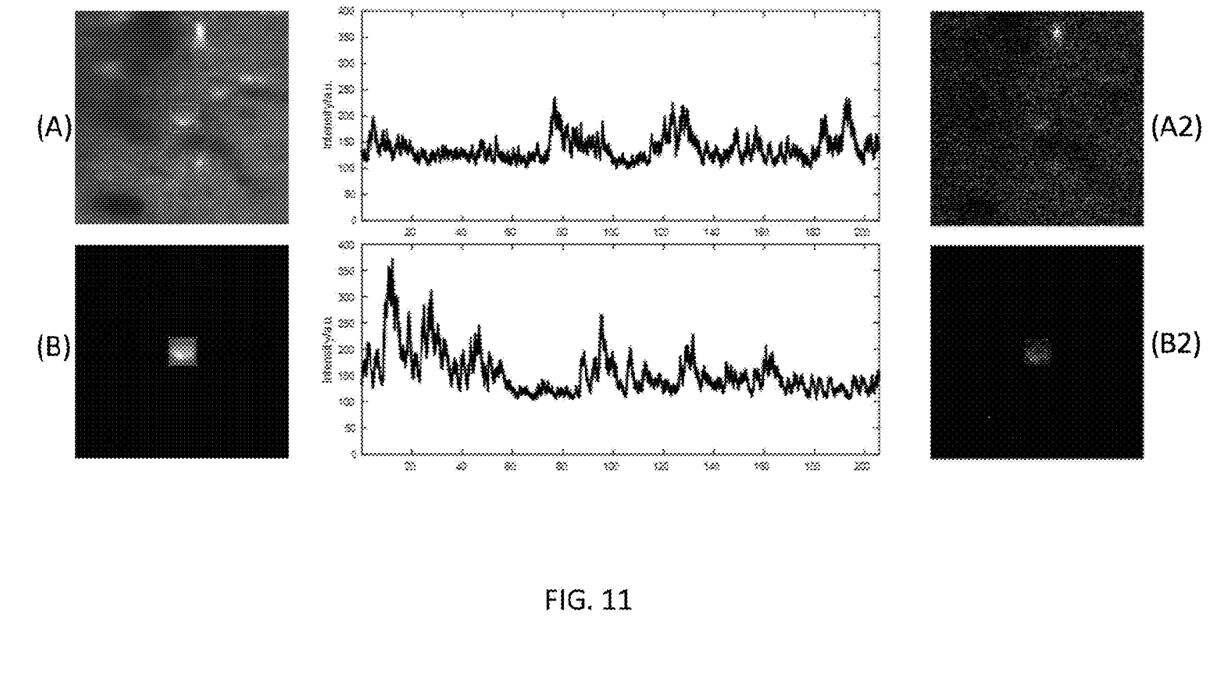
FIGS. 11A and 11B show a sixth data set of images resulting from use of the imaging system and method for adaptive illumination, in accordance with an embodiment.

Finally, turning to FIG. 11, there is shown a sixth data set of images resulting from use of the imaging system 100 and method for adaptive illumination described herein. The results shown in FIG. 11 were produced with activity imaging (GCaMP6) and a home-made microscope. Image (A) and Image (B) in FIG. 11 are both 62×62 μm, 256×256 pixels, at a depth of 498 μm taken at 15 frames per second. The power provided to Image (A) was 64 mW, while the power provided to the sample in Image (B) was 7 mW. Image (A2) was produced according to conventional method (i.e., without the imaging system 100 and method for AI disclosed herein). Image (B2) was obtained using the disclosed imaging system 100 and method for AI. As can be derived from the measurements shown in Tables 4 below, AI resulted in a power improvement factor of approximately 9.1.

TABLE 4

Comparative Imaging Measurements

|  | Uniform (without AI) | Non-uniform (with AI) |
| --- | --- | --- |
| Power on sample | 64 mW | 7 mW |
| Effective repetition rate | 4 MHz | ~0.25 MHz |
| Brightness when neuron not fire (mean pixel value) | 120 | 120 |

|  | Calculated Improvement | Measured Improvement |
| --- | --- | --- |
| Power (assuming same brightness) | ~8 | 9.1 |
| Brightness (assuming same average power) | ~64 | ~83 |

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. An imaging system for adaptive illumination, comprising:
   an excitation source having a modulator, which generates a pulse intensity pattern having a first wavelength when the excitation source receives a modulation pattern comprising a data sequence of at least a portion of a structural image of a sample;
   an amplifier configured to receive and amplify the pulse intensity pattern from the modulator;
   a frequency shift mechanism which shifts the first wavelength of the pulse intensity pattern to a second wavelength; and
   a laser scanning microscope, which receives the pulse intensity pattern having the second wavelength;
   wherein at least a portion of the structural image of the sample comprises one or more regions of interest to define the data sequence.

2. The imaging system of claim 1, wherein the frequency shift mechanism comprises a soliton self-frequency shift (SSFS).

3. The imaging system of claim 2, wherein the SSFS is in a photonic crystal rod.

4. The imaging system of claim 1, wherein the sample is a neuron.

5. The imaging system of claim 1, wherein the excitation source is an all-fiber chirped pulse amplifier.

6. The imaging system of claim 1, wherein the modulator is an electro-optic modulator.

7. The imaging system of claim 1, wherein each of the one or more regions of interest comprise a guard band.

8. The imaging system of claim 7, wherein a guard band size is selected to eliminate motion artifacts.

9. The imaging system of claim 7, wherein a guard band size is related to a range of motion for the laser scanning microscope during an imaging session.

10. The imaging system of claim 1, wherein the imaging system is configured to synchronize the pulse intensity pattern and the scanning of the laser scanning microscope.

11. The imaging system of claim 1, wherein the modulator is configured to cause the excitation source to only illuminate the one or more regions of interest.

12. The imaging system of claim 1, wherein the sample comprises one or more neurons and the one or more regions of interest are defined by one or more somas of the one or more neurons.

13. One or more non-transitory computer-readable media comprising instructions that, when executed by a machine, cause the machine to:
   generate a structural image of a sample;
   process the structural image to determine one or more regions of interest;
   convert the regions of interest into a data sequence representing a modulation pattern having a first wavelength;
   transmit the modulation pattern to an excitation source;
   encode, at the excitation source, the modulation pattern in time;
   amplify the modulation pattern with an amplifier at the excitation source;
   shift the first wavelength of the modulation pattern to a second wavelength; and
   transmit the modulation pattern having the second wavelength to a laser scanning microscope.

14. The one or more non-transitory computer-readable media of claim 13, wherein the instructions further cause the machine to conduct a raster scan of a sample.

15. The one or more non-transitory computer-readable media of claim 13, wherein to amplify the modulation pattern with an amplifier comprises to amplify the modulation pattern with an Erbium-doped-fiber amplifier.

16. The one or more non-transitory computer-readable media of claim 13, wherein to transmit the modulation pattern to an excitation source comprises to transmit the modulation pattern to a chirped pulse amplifier.

17. The one or more non-transitory computer-readable media of claim 13, wherein to generate a structural image of a sample comprises to generate a structural image of a neuron.

18. The one or more non-transitory computer-readable media of claim 17, wherein to process the structural image to determine one or more regions of interest comprises to process the structural image to determine one or more regions of interest defined by somas of the neuron.

19. An imaging system for adaptive illumination, comprising:
- an excitation source having a modulator, which generates a pulse intensity pattern having a first wavelength when the excitation source receives a modulation pattern comprising a data sequence of one or more regions of interest in a structural image of a sample;
- an amplifier configured to receive and amplify the pulse intensity pattern from the modulator;
- a frequency shift mechanism which shifts the first wavelength of the pulse intensity pattern to a second wavelength; and
- a laser scanning microscope, which receives the pulse intensity pattern having the second wavelength;
- wherein at least a portion of the structural image of the sample comprises one or more regions of interest to define the data sequence.

* * * * *